United States Patent [19]

Devic

[11] 4,379,092

[45] Apr. 5, 1983

[54] PROCESS FOR THE PREPARATION OF ANTHRAQUINONE AND ITS SUBSTITUTED DERIVATIVES

[75] Inventor: Michel Devic, Lyons, France

[73] Assignee: P C U K Produits Chimiques Ugine Kuhlmann, Courbevoie, France

[21] Appl. No.: 324,520

[22] Filed: Nov. 24, 1981

[30] Foreign Application Priority Data

Dec. 16, 1980 [FR] France ................. 80 26637

[51] Int. Cl.³ .................. C07C 50/18; C09B 1/00
[52] U.S. Cl. .................. 260/369; 260/384
[58] Field of Search .................. 260/369, 384

[56] References Cited

U.S. PATENT DOCUMENTS

| | | | |
|---|---|---|---|
| 1,515,325 | 11/1924 | Bailey ................. | 260/369 |
| 2,174,118 | 9/1939 | Calcott et al. ................. | 260/351 |
| 2,401,225 | 5/1946 | Caesar et al. ................. | 260/384 X |
| 2,842,562 | 7/1958 | Bloom et al. ................. | 260/369 |
| 2,871,244 | 1/1959 | Kamlet ................. | 260/369 |
| 2,967,187 | 1/1961 | Serres et al. ................. | 260/384 X |

FOREIGN PATENT DOCUMENTS

| | | | |
|---|---|---|---|
| 634987 | 8/1936 | Fed. Rep. of Germany | 260/369 |
| 2031430 | 2/1972 | Fed. Rep. of Germany | 260/369 |
| 2262007 | 9/1975 | France ................. | 260/369 |
| 2307786 | 11/1976 | France ................. | 260/369 |

*Primary Examiner*—Paul F. Shaver
*Attorney, Agent, or Firm*—Beveridge, DeGrandi & Kline

[57] ABSTRACT

A process for the preparation of anthraquinone compounds by condensation of phthalic anhydride with a benzene derivative wherein a mixture of hydrofluoric acid and boron trifluoride is utilized as catalyst.

7 Claims, No Drawings

PROCESS FOR THE PREPARATION OF ANTHRAQUINONE AND ITS SUBSTITUTED DERIVATIVES

The invention relates to a new process for the preparation of anthraquinone and its substituted derivatives of the general formula:

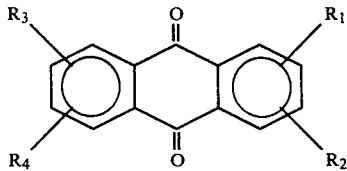

in which $R_1$, $R_2$, $R_3$ and $R_4$ each represent a hydrogen or halogen atom or a linear or branched alkyl group containing 1 to 5 carbon atoms. These compounds are used for dyestuffs, paper pulp industries and for the manufacture of hydrogen peroxide.

It is known that anthraquinone is produced industrially by oxidation of anthracene (BIOS 1148). This process, however, is dependent upon problems of supply of anthracene from coal tar. It has been proposed to prepare anthraquinone from 1,4-naphthoquinone and butadiene (British Pat. No. 895,620) but the processes for obtaining 1,4-naphthoquinone are complicated and costly (DOS 2,532,365 which corresponds to British Pat. No. 1,499,068).

Another much used industrial method enables anthraquinone and the substituted anthraquinones to be prepared from phthalic anhydride and benzene in the presence of aluminum chloride (U.S. Pat. No. 1,656,575), but this method has the disadvantage of the very considerable cost of the aluminum chloride which is consumed at the rate of 2 moles of aluminum chloride per mole of phthalic anhydride. In order to alleviate this disadvantage it has been proposed to react the gaseous mixture at high temperature over a solid catalyst based on a silico-aluminate (Japan Kokai Sho 49/30350 and Sho 49/95952) or else based on titanium oxide (Japan Kokai Sho 54/70252) but these processes impose the operation in the gaseous phase at high temperature and necessitate a complex installation with a costly investment.

The object of the present invention is to provide a catalyst which enables the condensation of phthalic anhydride and benzene to be effected at low temperature and in the liquid phase as when using aluminum chloride, but having the advantage of being able to be recovered after the reaction.

It has already been shown (Russian Pat. No. 189,445) that hydrofluoric acid catalyzes the condensation of phthalic anhydride with phenols. This reaction, however, takes place only with highly active benzene derivatives owing to the phenol function and no condensation is produced with benzene, chlorobenzene and the alkylbenzenes. Boron trifluoride does not exhibit sufficient catalytic activity to condense benzene with phthalic anhydride.

It has now been discovered, according to the present invention, that an equimolecular mixture of HF and $BF_3$ catalyzes the condensation of phthalic anhydride and benzene and does this, rather surprisingly, without causing cyclization of the benzoylbenzoic acid formed, therefore without liberating a molecule of water which would hydrolyze or hydrate $BF_3$ and thus make the recovery of the catalyst difficult. The fact that the equimolecular mixture of HF and $BF_3$ does not cause cyclization is quite unexpected since the cyclization of benzoyl-benzoic acid takes place in anhydrous HF (U.S. Pat. No. 2,174,118).

The present invention therefore relates to a process for the preparation of compounds of general formula (I) which comprises reacting phthalic anhydride which can be substituted of the formula:

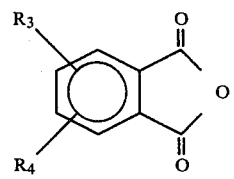

with a benzene compound of the general formula:

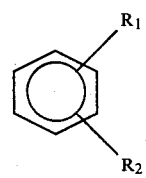

in which $R_1$, $R_2$, $R_3$ and $R_4$ have the same definitions as above in the presence of a catalyst, characterized in that the latter consists of a mixture of hydrofluoric acid and boron trifluoride and that the o-benzoyl benzoic acid thus obtained of the general formula:

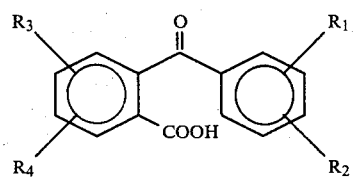

in which $R_1$, $R_2$, $R_3$ and $R_4$ have the same definitions as above, is converted into a compound of formula (I) according to the process known per se.

The amount of $BF_3$ must be greater than 3 moles per mole of phthalic anhydride; the preferred ratio is between 5 and 20 moles of $BF_3$ per mole of phthalic anhydride. The amount of HF must be greater than 2 moles per mole of phthalic anhydride. The preferred ratio is between 5 and 15 moles. The molar ratio HF to $BF_3$ must be near to 1, when the amount of catalyst is lower than 15 (moles of HF+moles of $BF_3$<15). The preferred ratio is between 0.6 and 1.5. For amounts of $BF_3$ greater than 10 moles per mole of phthalic anhydride, the preferred ratio is between 0.2 and 1.

Since the catalyst also takes the place of a solvent for the reaction, it must be used in sufficient quantity to make the reaction mass fluid, for example, from 5 to 20 moles of $BF_3$ per mole of phthalic anhydride. This amount may be reduced by the use of a third solvent which is inert under the conditions of the reaction. As inert solvents methylene chloride and liquid $CO_2$ may be mentioned.

The phthalic anhydride and the aromatic derivative of formula (III) are employed at the rate of 0.9 to 1.2 moles of compound (III) per mole of phthalic anhydride. In order to reduce the formation of by-products, it is preferred to use 1 to 1.1 mole of benzene compound per mole of phthalic anhudrice. Excess of benzenic compound favors the formation of the phenyl-phthalic derivatives of the general formulas:

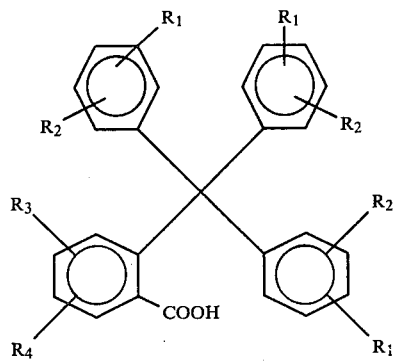
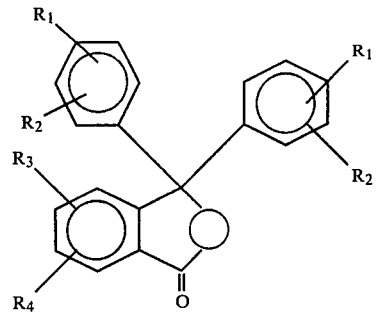

The reaction may be effected at temperatures from −60° C., to +30° C., the preferred temperature being from −40° C. to 0° C. A temperature over 30° C. increases the quantity of by-products of the phenyl-phthalide type. The length of reaction is between 5 and 60 minutes according to the temperature. The reaction takes place under a pressure of 5 to 60 bars according to the temperature.

At the end of the reaction the greater part of catalyst is recovered by distillation under reduced pressure. The pure o-benzoyl benzoic acid is obtained by extraction of the crude mixture with boiling water, followed by re-crystallization by cooling. The impurities from the reaction form a phase immiscible with water and can be eliminated by decantation or by filtration on an absorbent support.

The pure o-benzoyl benzoic acid can be obtained by treating the reaction medium, after evaporation of the catalyst under vacuum, by means of a sodium hydroxide solution and adding an inorganic acid to reprecipitate the acid.

The o-benzoyl benzoic acid of general formula (IV) can be converted into the anthraquinone of general formula (I) by heating in concentrated sulfuric acid or by any other means of cyclization known in the art. As in the production of intermediate anthraquinone compounds for dyes, the cyclization may take place in the course of the sulfonation and nitration reactions which take place in a cyclizing medium, for example $H_2SO_4$ or HF.

The following examples illustrate the present invention without it being limited thereto. In the examples and throughout the specification and claims, all parts and percentages are by weight unless otherwise specified.

EXAMPLE 1

7.4 g of phthalic anhydride and 3.9 of benzene were charged at ambient temperature into a stainless steel autoclave. The autoclave was cooled by liquid nitrogen and 10 g of HF and 37.4 g of $BF_3$ were introduced. The autoclave was heated to 20° C. and the pressure raised to 47 bars. The temperature was maintained at 20° C. for 15 minutes and the product degassed under reduced pressure in order to recover the catalyst. After washing with cold water, 10 g of crude o-benzoyl benzoic acid were obtained titrating 74.4% and containing 0.5% of anthraquinone, thus a chemical yield of 66%. After purification by extraction with 600 $cm^3$ of boiling water, then crystallization by cooling to 20° C., o-benzoyl benzoic acid titrating 98.4% was obtained.

5 g of the purified benzoyl benzoic acid were heated at 100° C. for 2 hours in 50 g of fuming sulfuric acid (20% $SO_3$). The mixture was run on 350 $cm^3$ of water and ice and the precipitate obtained was filtered, washed and dried. 4.2 g of anthraquinone were obtained.

EXAMPLE 2 (Comparative)

The procedure was as in Example 1, but with 7.4 g of phthalic anhydride, 39 g of benzene, 8.5 g of $BF_3$ and no HF. The mixture was maintained at 60° C. for 4 hours under 22 bars pressure. After evaporation in vacuo of the catalyst, the residue was washed with cold water and then dried. 5.6 g of product were obtained consisting essentially of phthalic acid.

EXAMPLE 3 (Comparative)

The procedure was as in Example 1, but with 7.4 g of phthalic anhydride, 39 g of benzene, 10 g of HF and no $BF_3$. The mixture was maintained at 100° C. for 4 hours under 5 bars pressure. After evaporation in vacuo of the catalyst, the residue was washed with cold water, then dried. 7.01 g of product were obtained consisting essentially of phthalic acid.

EXAMPLE 4 (Comparative)

The procedure was exactly as in Example 1, but double the quantity of benzene was added. 7.5 g of a product were obtained containing only 0.3% of benzoyl benzoic acid and 1% of anthraquinone.

EXAMPLE 5

7.4 g of phthalic anhydride and 5.3 g of ethylbenzene were charged at ambient temperature into a stainless steel autoclave. The autoclave was cooled by liquid nitrogen and 10 g of HF and 37.4 g of $BF_3$ were introduced. The autoclave was heated to about 0° C. in order to take the pressure to 20 bars. This pressure was maintained for 15 minutes, then the product was degassed under reduced pressure in order to recover the catalyst. The residue was washed with cold water and dried.

9.4 g of crude ethyl-benzoyl-benzoic acid were obtained titrating 81%, thus a chemical yield of 60%. After purification by extraction with boiling water, then crystallization by cooling, the ethyl-benzoyl-benzoic acid was obtained. 5 g of this product were heated in 20% oleum according to Example 1, 3.75 g of 2-ethyl-anthraquinone were obtained.

EXAMPLE 6

22.2 g of phthalic anhydride (0.15 mole) were charged at ambient temperature into a stainless steel autoclave. The autoclave was cooled with liquid nitrogen. 30 g of HF (1.5 mole) and 102 g of BF$_3$ (1.5 moles) were introduced; the temperature was brought to $-40°$ C. and 12.9 g of benzene (0.165 mole) were introduced during 15 minutes. A pressure of 16 bars was maintained at $-40°$ C. for 1 hour; after decompression at $-40°$ C., degasification was performed to evaporate HF and BF$_3$. The solid obtained was o-benzoyl benzoic (O.B.B.) acid containing small amounts of HF and BF$_3$.

The crude O.B.B. acid was dissolved in the cold in 10% caustic soda. The solution was filtered. The O.B.B. acid was precipitated by the addition of concentrated hydrochloric acid. There were obtained 30.6 g of O.B.B. acid of 94% purity (chemical yield, 85%). 5 g of this O.B.B. acid were heated at 100° C. for 2 hours in 50 g of fuming sulfuric acid (20% SO$_3$). The mixture was poured into 350 cm$^3$ of water. The precipitate obtained was filtered, dried and washed. There were obtained 4.10 g of anthraquinone of 99.7% purity.

EXAMPLE 7

Operating as in Example 6, but with more BF$_3$ and less HF, that is, 15 g of HF (0.75 mole) and 153 g of BF$_3$ (2.25 moles). 30.0 g of O.B.B. acid were obtained of 93.7% purity. 5 g of this O.B.B. acid yielded 4.10 g of anthraquinone when heated in sulfuric acid.

EXAMPLE 8

Operating as in Example 7, but replacing the benzene by 13.55 g of monochlorobenzene (0.165 mole), there were obtained 12.6 g of pure chlorobenzoyl-benzoic acid (chemical yield 32%). On heating at 150° C. in 100% sulfuric acid, the chlorobenzoylbenzoic acid obtained yielded 2-chloro-anthraquinone.

EXAMPLE 9

Operating as in Example 6 but with a greater quantity of catalyst, e.g., 45 g of HF (2.25 moles) and 153 g of BF$_3$ (2.25 moles), there were obtained 40.1 g of crude O.B.B. acid of 76.2% purity (chemical yield 90%). 5 g of this O.B.B. acid, on heating in sulfuric acid, yielded 3.35 g of anthraquinone.

EXAMPLE 10

Operating as in Example 7, but replacing the benzene by 17.5 g of ethylbenzene (0.165 mole), there were obtained 33.7 g of ethylbenzoyl-benzoic acid (0.165 mole) of 96.2% purity (chemical yield 83%). 5 g of this ethylbenzoyl-benzoic acid, on heating in sulfuric acid, yielded 4 g of 2-ethyl-anthraquinone.

EXAMPLE 11

Operating as in Example 8 but replacing the benzene with 15.4 g of toluene (0.165 mole), there were obtained 30 g of methylbenzoyl-benzoic acid (chemical yield 83.4%). 5 g of this methyl-O.B.B. acid, on heating in sulfuric acid, yielded 4.1 g of 2-methyl-anthraquinone.

EXAMPLE 12

22.2 g of phthalic anhydride (0.15 mole) were charged into a stainless steel autoclave at ambient temperature with 10 cm$^3$ of methylene chloride. The autoclave was cooled with liquid nitrogen. 30 g of HF (1.5 mole) and 102 g of BF$_3$ (1.5 mole) were introduced. The temperature was brought to $-40°$ C. and 12.9 g of benzene (0.165 mole) were introduced during 15 minutes. The temperature was maintained at $-40°$ C. for one hour under 15 bars pressure, followed by decompression and degasification under vacuum to evaporate HF, BF$_3$ and CH$_2$Cl$_2$; 10% caustic soda was then added to give a pH of 9. The solution was filtered, then acidified by addition of concentrated HCl. The O.B.B. acid precipitated in the form of very pure white crystals. The whole of the O.B.B. acid obtained was treated for 1 hour at 150° C. in 100% sulfuric acid. After cooling and dilution with water, 25.6 g of anthraquinone of 99.8% purity were obtained, i.e., an overall chemical yield of 82%.

EXAMPLE 13

Operating as in Example 12, but replacing the methylene chloride by 15 g of CO$_2$, which was liquid under the reaction conditions, there were obtained 29.15 g of O.B.B. acid, i.e., a chemical yield of 86%.

EXAMPLE 14

22.2 g of phthalic anhydride (0.15 mole) and 17.5 g of para-xylene (0.165 mole) were charged at ambient temperature into a stainless steel autoclave. The autoclave was cooled with liquid nitrogen, and 15 g of HF (0.75 mole) and 102 g (1.5 moles) of BF$_3$ were introduced.

The temperature was allowed to rise to $-40°$ C. and was maintained at $-40°$ C. for 30 minutes, under a pressure of 17 bars. Decompression and degassing under vacuum were performed to evaporate HF and BF$_3$; 10% caustic soda was then added to give a pH of 9. The solution was filtered, and was then acidified by addition of concentrated hydrochloric acid. Dimethylbenzoylbenzoic acid precipitated in the form of very pure white crystals. 32.9 g of this acid were obtained (chemical yield, 86.4%). 4 g of this dimethyl-O.B.B. acid, on being heated in 100% sulfuric acid, yielded 3.28 g of 1,4-dimethyl anthraquinone.

What is claimed is:

1. Process for the preparation of anthraquinone compounds of the general formula:

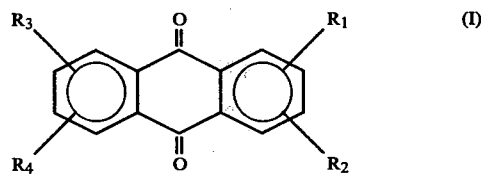

in which R$_1$, R$_2$, R$_3$, R$_4$ represent hydrogen, halogen or a linear or branched alkyl containing 1 to 5 carbon atoms which comprises reacting a phthalic anhydride or substituted phthalic anhydride of the formula:

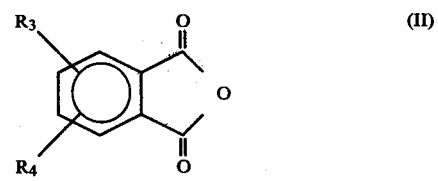

with a benzene compound of the formula:

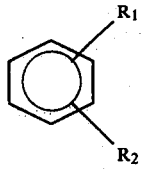 (III)

wherein $R_1$, $R_2$, $R_3$, and $R_4$ have the same definition as above, in the presence of a catalyst mixture of hydrofluoric acid and boron trifluoride, and converting the thus obtained o-benzoyl benzoic acid of the formula:

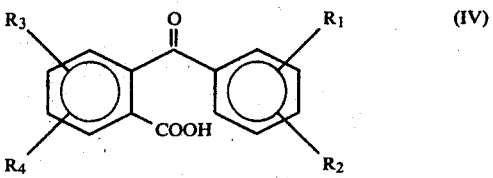 (IV)

in which $R_1$, $R_2$, $R_3$, and $R_4$ have the same definition as above, into the compound of formula (I) by cyclization.

2. The process according to claim 1 wherein the $HF/BF_3$ ratio is between 0.2 and 1.5.

3. The process according to claim 2 wherein from 0.9 to 1.2 moles of the compound of formula (I) are used per mole of phthalic anhydride.

4. The process according to claim 1, 2 or 3 wherein the condensation is carried out at a temperature ranging from $-60°$ C. to $+30°$ C. and a pressure ranging from 5 to 60 bar.

5. The process according to claim 4 wherein the condensation is carried out at a pressure between 15 and 20 bar and at a temperature of $-40°$ C.

6. The process according to claim 1 wherein the o-benzoyl benzoic acid of formula (IV) is extracted with boiling water from the reaction mixture.

7. The process according to claim 1 wherein from 5 to 20 moles of $BF_3$ and of HF are utilized per mole of phthalic anhydride.

* * * * *